United States Patent
Terashi et al.

(10) Patent No.: US 12,357,984 B2
(45) Date of Patent: Jul. 15, 2025

(54) ORGANIC SOLVENT PURIFICATION METHOD AND PURIFICATION SYSTEM

(71) Applicant: ORGANO CORPORATION, Tokyo (JP)

(72) Inventors: Ryosuke Terashi, Tokyo (JP); Kyosuke Yamada, Tokyo (JP)

(73) Assignee: ORGANO CORPORATION, Tokyo (JP)

( * ) Notice: Subject to any disclaimer, the term of this patent is extended or adjusted under 35 U.S.C. 154(b) by 167 days.

(21) Appl. No.: 17/763,088

(22) PCT Filed: Sep. 15, 2020

(86) PCT No.: PCT/JP2020/034926
§ 371 (c)(1),
(2) Date: Mar. 23, 2022

(87) PCT Pub. No.: WO2021/065483
PCT Pub. Date: Apr. 8, 2021

(65) Prior Publication Data
US 2022/0371000 A1 Nov. 24, 2022

(30) Foreign Application Priority Data
Sep. 30, 2019 (JP) .................................. 2019-179841

(51) Int. Cl.
*B01J 47/026* (2017.01)
*B01D 1/02* (2006.01)
(Continued)

(52) U.S. Cl.
CPC .............. *B01J 47/026* (2013.01); *B01D 1/02* (2013.01); *B01D 61/362* (2013.01);
(Continued)

(58) Field of Classification Search
None
See application file for complete search history.

(56) References Cited

U.S. PATENT DOCUMENTS

2014/0163264 A1 6/2014 Takahashi et al.
2017/0158635 A1 6/2017 Terashi et al.

FOREIGN PATENT DOCUMENTS

CN 106132516 A 11/2016
FR 580 531 A 1/1960
(Continued)

OTHER PUBLICATIONS

Office Action issued Jul. 1, 2023 in family member Chinese patent application No. 202080068990.6 with English language translation.
(Continued)

*Primary Examiner* — Krishnan S Menon
(74) *Attorney, Agent, or Firm* — GREENBLUM & BERNSTEIN, P.L.C.

(57) ABSTRACT

A purification method for separating and purifying an organic solvent from a liquid mixture of an organic solvent and water, the organic solvent having a boiling point of more than 100° C. at 1 atm, includes the steps of: passing the liquid mixture through a first ion exchange device; supplying the liquid mixture discharged from the first ion exchange device to a pervaporation device to selectively separate water component; supplying the organic solvent recovered from the concentration side of the pervaporation device to an evaporator to obtain a purified organic solvent; and passing, through the second ion exchange device, a portion of liquid containing the organic solvent and flowing at a first position subsequent to the first ion exchange device. The liquid discharged from the second ion exchange device is returned to a second position which is at a preceding stage of the pervaporation device.

16 Claims, 4 Drawing Sheets (51) Int. Cl.
*B01D 61/36* (2006.01)
*B01J 47/04* (2006.01)
*B01J 47/10* (2017.01)
*B01J 47/14* (2017.01)
*C07B 63/00* (2006.01)
*C07D 207/267* (2006.01)

(52) U.S. Cl.
CPC ......... *B01D 61/365* (2022.08); *B01D 61/368* (2013.01); *B01J 47/04* (2013.01); *B01J 47/10* (2013.01); *B01J 47/14* (2013.01); *C07B 63/00* (2013.01); *C07D 207/267* (2013.01)

(56) References Cited

FOREIGN PATENT DOCUMENTS

| | | | |
|---|---|---|---|
| JP | 62-193652 A | 8/1987 | |
| JP | 11-5090 A | 1/1999 | |
| JP | 2005-247770 A | 9/2005 | |
| JP | 2013-18747 A | 1/2013 | |
| JP | 2014055120 A * | 3/2014 | |
| JP | 2014-144936 A | 8/2014 | |
| JP | 2014-144937 A | 8/2014 | |
| JP | 2014-144940 A | 8/2014 | |
| JP | 2014144938 A * | 8/2014 | |
| JP | 2015-71139 A | 4/2015 | |
| JP | 2016-30233 A | 3/2016 | |
| JP | 2016030233 A * | 3/2016 | ........... B01D 15/363 |
| JP | 2019-141793 A | 8/2019 | |
| KR | 10-2016-0104716 A | 9/2016 | |

OTHER PUBLICATIONS

International Search Report and Written Opinion of the International Searching Authority issued in International Patent Application No. PCT/JP2020/034926, dated Nov. 17, 2020, along with an English translation thereof.
Supplementary European Search Report issued Jan. 5, 2024 in European family member patent application No. 20872475.7.
Office Action that issued in corresponding Korean Patent Application No. 10-2022-7001220, dated Jul. 26, 2024, along with English translation thereof.

* cited by examiner

ORGANIC SOLVENT PURIFICATION METHOD AND PURIFICATION SYSTEM

TECHNICAL FIELD

The present invention relates to a purification method and a purification system for purifying an organic solvent having a boiling point of more than 100° C. at 1 atm (i.e., 0.1013 MPa), such as N-methyl-2-pyrrolidone (hereinafter also referred to as NMP). In particular, the present invention relates to a purification method and a purification system suitable for purifying and reusing an organic solvent which contains water and is recovered from equipment or a process using the organic solvent.

BACKGROUND ART

Some organic solvents have a high solubility in water and a boiling point above 100° C. at 1 atm, that is, those having a higher boiling point than water. When such a water-soluble organic solvent is used, and then recovered and reused, a liquid mixture of the organic solvent and water is often recovered. Therefore, it is necessary to separate and purify the organic solvent to be reused from the liquid mixture. In addition to the organic solvent and water, the recovered liquid mixture may contain hardly-volatile impurities such as ionic substances and fine particles, and further, an organic substance or an organic impurity different from the organic solvent to be reused.

NMP, which is one of organic solvents having a high solubility in water and a boiling point of more than 100° C. at 1 atm, is widely used as a dispersion medium, for example, in manufacturing an electrode, particularly a positive electrode, of a lithium ion secondary battery (LIB). The main constituent materials of each electrode, i.e., a positive electrode and a negative electrode, of the lithium ion secondary battery are an electrode active material, a collector, and a binder. As a binder, one obtained by dissolving polyvinylidene fluoride (PVDF) in NMP as a dispersion medium is generally used. Electrodes are generally produced by applying a slurry of a mixture of an electrode active material and a binder onto a collector and vaporizing NMP by heating in air, i.e., in the presence of oxygen. NMP used in the manufacturing process of the lithium ion secondary battery and vaporized can be recovered in the form of an aqueous NMP solution by a recovery device such as a water scrubber, for example. The recovered NMP can be used again in a manufacturing process of a lithium ion secondary battery or the like by removing water and impurities contained therein. In addition to the manufacturing process of a lithium ion secondary battery, NMP is also used in various fields as an organic solvent miscible with water, and in such a field, it is also required to recover and reuse NMP after use.

Recovery of NMP from an aqueous NMP solution is one of the applications of the method for separating and recovering an organic solvent from a liquid mixture of the organic solvent and water. As a method of separating and recovering an organic solvent from a liquid mixture of the organic solvent and water, a pervaporation (PV) method is known. The pervaporation method is an excellent method for separating water from organic solvents having a boiling point higher than water. When NMP is recovered from an aqueous NMP solution using the pervaporation method, a separation membrane (i.e., a pervaporation membrane) having an affinity for water component is used. The aqueous NMP solution is brought to flow toward a supply side of the separation membrane, and a pressure is reduced or an inert gas is brought to flow on a permeation side of the separation membrane. As a result, separation is performed due to the difference in permeation rates between water and NMP in the separation membrane, and a water-rich component appears on the permeation side of the separation membrane. As a separation membrane through which water component is brought to pass, for example, a zeolite membrane is used. If only water component is transferred to the permeation side by the separation membrane, NMP remains on the side of the separation membrane to which the liquid mixture is supplied, that is, on a concentration side, so that NMP can be recovered from the concentration side.

Patent Literature 1 discloses an NMP purification system which uses a pervaporation device and in which ion exchange devices are provided at a preceding stage and a subsequent stage of the pervaporation device, as a system for obtaining purified NMP by separating NMP from a liquid mixture of NMP and water. Patent Literature 2 discloses that an evaporator is provided at a subsequent stage of a pervaporation device, in order to remove ionic impurities and fine particles from NMP purified using the pervaporation device to obtain further high-purity NMP. Patent Literature 2 further discloses that an ion exchange device is provided at a preceding stage of the pervaporation device when a water-containing NMP with a large amount of ionic impurities is purified or when an ionic impurity concentration in the purified NMP is brought to be extremely low. As an evaporator used for removing ionic impurities and fine particles from NMP, for example, a vacuum evaporator of such as a liquid film flow-down type, a flash type, or a calandria type can be used.

CITATION LIST

Patent Literature

Patent Literature 1: JP 2013-18747 A
Patent Literature 2: JP 2016-30233 A

SUMMARY OF THE INVENTION

Technical Problem

An organic solvent recovered from equipment or a process using the organic solvent may contain an organic impurity having a boiling point close to that of the organic solvent. It is difficult to remove such an organic impurities by simply using an evaporator or the like. For example, NMP recovered from equipment or a process using NMP may contain an organic impurity having a boiling point close to that of NMP. In the purification system described in Patent Literature 2, since the number of theoretical plates of the vacuum evaporator is small, an organic impurity having a boiling point close to that of NMP cannot be sufficiently removed, and the organic impurity remains in the purified NMP. If such purified NMP is reused and recovered, and the recovered NMP is purified and reused repeatedly, the concentration of the organic impurity in the purified NMP gradually increases. As an example of an organic impurity having a boiling point close to that of NMP, there is N-methylsuccinimide. The boiling point at 1 atm is 235° C. for N-methylsuccinimide compared to 202° C. for NMP.

It is an object of the present invention to provide a purification method and a purification system for an organic solvent, which can prevent an increase in concentration of organic impurities in the purified organic solvent even when recovery, purification and reuse of the organic solvent are repeated.

Solution to Problem

The present inventors have studied process with an ion exchange resin as a method of removing organic impurities mixed in organic solvents. As a result, the present inventors have found that various organic impurities in organic solvents could be removed by ion exchange resin regardless of the presence or absence of coexisting water component. However, it has also been found that a long time is required for adsorbing organic impurities to an ion exchange resin as compared with a case where an ionic impurities are adsorbed on the ion exchange resin. When an attempt is made to remove organic impurities by passing the entire amount of the liquid mixture of water and an organic solvent, which is a target of purification, through an ion exchange resin, since the residence time in the ion exchange resin must be prolonged, it is necessary to use a large amount of ion exchange resin and to increase the residence time as compared with a case where only ionic impurities are removed. The purpose of removing organic impurities is to prevent the concentration of organic impurities from increasing when, for example, recovery, purify and reuse of an organic solvent are repeated. From this viewpoint, when the organic impurities are removed from the organic solvent, only the organic impurities of the portion which has been newly generated by reuse or re-purification may be removed, and therefore, the total amount of the organic solvent does not necessarily have to be subjected to ion exchange treatment for removal of the organic impurities.

Therefore, the purification method according to the present invention is a purification method for separating and purifying an organic solvent from a liquid mixture of the organic solvent and water, the organic solvent having a boiling point of more than 100° C. at 1 atm, the purification method comprising: a first ion exchange step of passing the liquid mixture into a first ion exchange resin; a dehydration step of selectively separating water component from the liquid mixture by supplying the liquid mixture discharged from the first ion exchange step to a pervaporation device having a pervaporation membrane; an evaporation step of supplying the organic solvent recovered from a concentration side of the pervaporation membrane to an evaporator to vaporize, and obtaining the organic solvent which has been purified; and a second ion exchange step of treating a portion of liquid which contains the organic solvent and flows at a first position subsequent to the first ion exchange step, and wherein liquid discharged from the second ion exchange step is returned to a second position, which is at a preceding stage of the dehydration step.

The purification system according to the present invention is a purification system for separating and purifying an organic solvent from a liquid mixture of the organic solvent and water, the organic solvent having a boiling point of more than 100° C. at 1 atm, the purification system comprising: a first ion exchange device to which the liquid mixture is supplied; a pervaporation device having a pervaporation membrane in which the liquid mixture passed through the first ion exchange device is supplied to selectively separate water component from the liquid mixture; an evaporator vaporizing the organic solvent recovered from a concentration side of the pervaporation membrane and generating the organic solvent which has been purified; and a second ion exchange device to which a portion of liquid containing the organic solvent and flowing at a first position subsequent to the first ion exchange device is suppled, wherein liquid discharged from the second ion exchange device is returned to a second position which is at a preceding stage of the pervaporation device in the purification system.

Advantageous Effects of Invention

According to the present invention, it is possible to prevent an increase in the concentration of organic impurities contained in the purified organic solvent even when the recovery, purify and reuse of the organic solvent are repeated.

DESCRIPTION OF EMBODIMENTS

Figure 1:
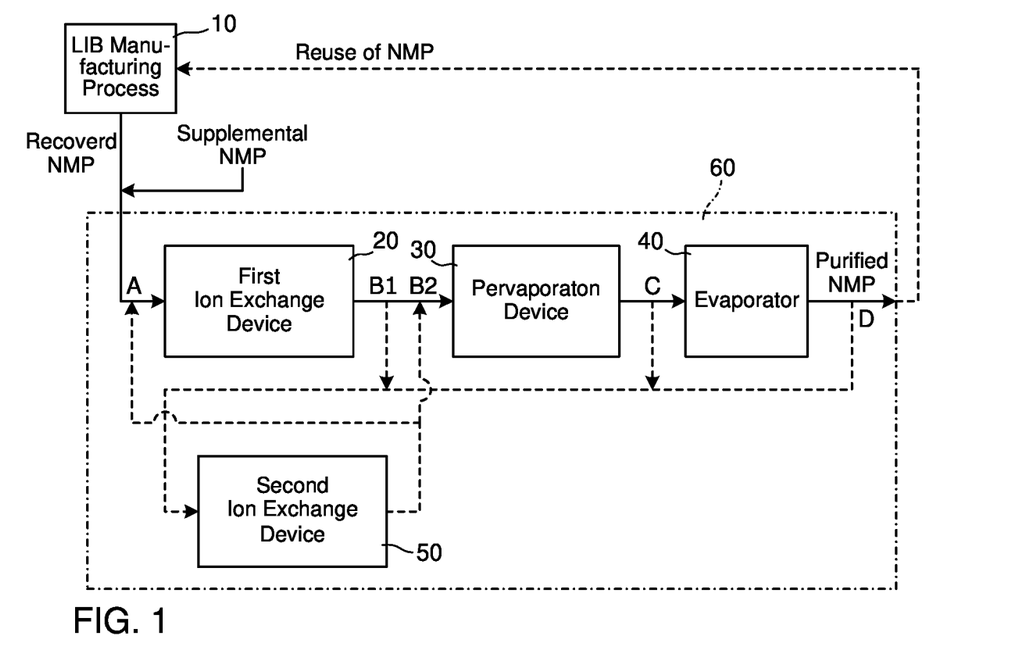
FIG. 1 is a diagram illustrating a basic aspect of a purification method of an organic solvent according to the present invention.

Next, preferred embodiments of the present invention will be described with reference to the accompanying drawings. FIG. 1 illustrates a basic aspect of a purification method for an organic solvent according to the present invention. The purification method according to the present invention is one in which an organic solvent having a boiling point of more than 100° C. at 1 atm (0.1013 MPa) is separated and purified from a liquid mixture of the organic solvent and water. This purification method can be preferably used, for example, when NMP discharged from lithium ion secondary battery (LIB) manufacturing process 10 is recovered, and the recovered NMP is purified and the obtained purified NMP is reused in lithium ion secondary battery manufacturing process 10. Since, for example, a water scrubber is used in recovery of NMP, the recovered NMP is a liquid mixture of water and NMP, the liquid mixture containing, for example, 10 to 20% by mass of water. Therefore, when the purification method according to the present invention is applied to recovered NMP, dehydration is performed on the liquid mixture which is the recovered NMP, and impurities in NMP are removed. Hereinafter, a case in which NMP is used as an organic solvent will be described, but an organic solvent to which the present invention is applicable is not limited to NMP. The present invention can be applied to an organic solvent having a boiling point at 1 atm (0.1013 Mpa) higher than the boiling point of water (100° C.), preferably an organic solvent having a boiling point at 1 atm of 120° C. or more, which is usual operation temperature of a pervaporation device. Examples of such organic solvents are shown in Table 1. In Table 1, boiling points are values at 0.1013 MPa.

TABLE 1

| Name | Boiling point (° C.) |
| --- | --- |
| N-methyl-2-pyrrolidone (NMP) | 202 |
| 1-methoxy-2-propanol (PGME) | 120 |
| Propylene glycol-1-monomethyl ether-2-acetate (PGMEA) | 146 |
| Pyridine | 115 |
| Dimethyl sulfoxide (DMSO) | 189 |
| Monoethanolamine (MEA) | 170 |
| N,N-dimethylformamide (DMF) | 153 |
| γ-butyrolactone (GBL) | 204 |
| Dimethylacetamide (DMA) | 165 |

As an organic solvent to which the present invention is applicable, an organic solvent which does not form an azeotropic mixture with water is more preferred. In the organic solvents shown in Table 1, organic solvents excluding PGME, PGMEA and pyridine are organic solvents which do not form an azeotrope mixture with water.

In the aspect shown in FIG. 1, the recovered NMP may be supplemented with a new liquid of NMP or supplemental NMP to replenish the amount of NMP loss in the course of purification or reuse of NMP. Then, as a first ion exchange step, in order to remove ionic impurities contained therein, the recovered NMP, i.e., the liquid mixture, is passed through first ion exchange device 20 in which an ion exchange resin such as a styrene-based strongly basic anion exchange resin is filled as a first ion exchange resin. The liquid mixture discharged from first ion exchange device 20 is then supplied as a dehydration step to pervaporation device 30 equipped with a pervaporation membrane, and water component is selectively separated. As a result, dehydrated NMP is discharged from the concentration side of the pervaporation membrane of pervaporation device 30, and this dehydrated NMP is supplied to evaporator 40. In evaporator 40, as an evaporation step, NMP is purified by vaporization, and purified NMP is discharged from evaporator 40. In other words, in evaporator 40, a hardly-volatile component such as fine particles or ionic impurities (e.g., salts) contained in NMP is removed from NMP. Colored impurities in NMP can also be removed by evaporator 40. As evaporator 40, for example, a vacuum evaporator can be used. The purified NMP obtained from evaporator 40 can be condensed and then reused, for example, in lithium ion secondary battery manufacturing process 10.

Further, this purification method has, as a second ion exchange step, a step of passing a portion of the liquid which containing NMP and flowing at a first position, which is a position subsequent to first ion exchange device 20, through second ion exchange device 50. Second ion exchange device 50 also performs ion exchange treatment using an ion exchange resin, and the ion exchange resin used in second ion exchange device 50 is also referred to as a second ion exchange resin. As the second ion exchange resin, when purification of NMP is carried out, for example, a mixture of a strongly acidic cation exchange resin of the H form and a strongly basic anion exchange resin of the OH form in a mixed bed, or a strongly basic anion exchange resin of the OH form in a single bed can be preferably used. The matrix structure of the second ion exchange resin is preferably styrene-based. The structure of the second ion exchange resin may be any of MR (macroreticular) type, MP (macroporous) type, and gel type. Examples of ion-exchange resins that meet such requirements include ORLITE® DS-5 and Amberlite® IRA400 (OH). Then, the liquid discharged from second ion exchange device 50 is returned to a second position, which is at a preceding stage of pervaporation device 30 and at a position subsequent to the first position. In FIG. 1, with respect to the path of NMP flow, the position at which the recovered NMP, i.e., the liquid mixture, is supplied to first ion exchange device 20 is indicated by "A," the position between first ion exchange device 20 and pervaporation device 30 is indicated by "B1" and "B2," the position between pervaporation device 30 and evaporator 40 at which the dehydrated NMP flows is indicated by "C," and the position at which the purified NMP discharged from evaporator is indicated by "D." With respect to the NMP flow, position B1 is upstream of position B2. A portion of the liquid flowing in any of positions B1, C and D is supplied to second ion exchange device 50. The supplied liquid is passed through second ion exchange device 50, and then returned to any of positions A and B2. A point which is any of positions B1, C and D described-above and at which a portion of the liquid flowing therethrough is sent to second ion exchange device 50 is referred to as a branch point.

In the example shown in FIG. 1, purification system 60 is configured by first ion exchange device 20, pervaporation device 30, evaporator 40 and second ion exchange device 50.

As will be apparent from Reference Examples described later, various organic impurities in NMP can be removed by an ion exchange resin regardless of the presence or absence of coexisting water component, but it takes a long time to adsorb organic impurities to an ion exchange resin as compared with a case where ionic impurities are adsorbed on the ion exchange resin. Therefore, in this aspect, the ionic impurities in the liquid mixture are mainly removed in first ion exchange device 20, and a portion of the NMP-containing liquid flowing downstream of first ion exchange device 20 is extracted and guided to second ion exchange device 50, thereby removing the organic impurities at second ion exchange device 50. Since water is generated from the ion exchange resin by an ion exchange reaction caused by adsorption of organic impurities on the ion exchange resin in second ion exchange device 50, and this water is mixed into NMP, the liquid that has passed through second ion exchange device 50 needs to be returned to a position which is at a preceding stage of pervaporation device 30 which is the dehydration means.

Since adsorbing organic impurities to the ion exchange resin takes a longer time than the case of adsorbing ionic impurities, it is necessary to set the distribution ratio of the liquid to second ion exchange device 50 at the branch point and the amount of the ion exchange resin to be filled in second ion exchange device 50 so that the residence time of the liquid in second ion exchange device 50 becomes longer than the residence time in first ion exchange device 20. When liquid is flowed through second ion exchange device 50, the liquid may be constantly supplied at a certain distribution ratio with respect to second ion exchange device 50 at the branch point. Alternatively, after stopping the production of the purified NMP at every fixed time or every time the purity decrease in the purified NMP is detected, entirety of the liquid flowing through the branch point may be supplied to second ion exchange device 50 to remove the organic impurities, and then the liquid from which the organic impurities have been removed may be returned to any of positions A and B2.

Next, the present invention will be described in more detail by specific embodiments. The purification system of the first to third embodiments described below specifically realizes the purification method according to the present invention described with reference to FIG. 1.

First Embodiment

Figure 2:
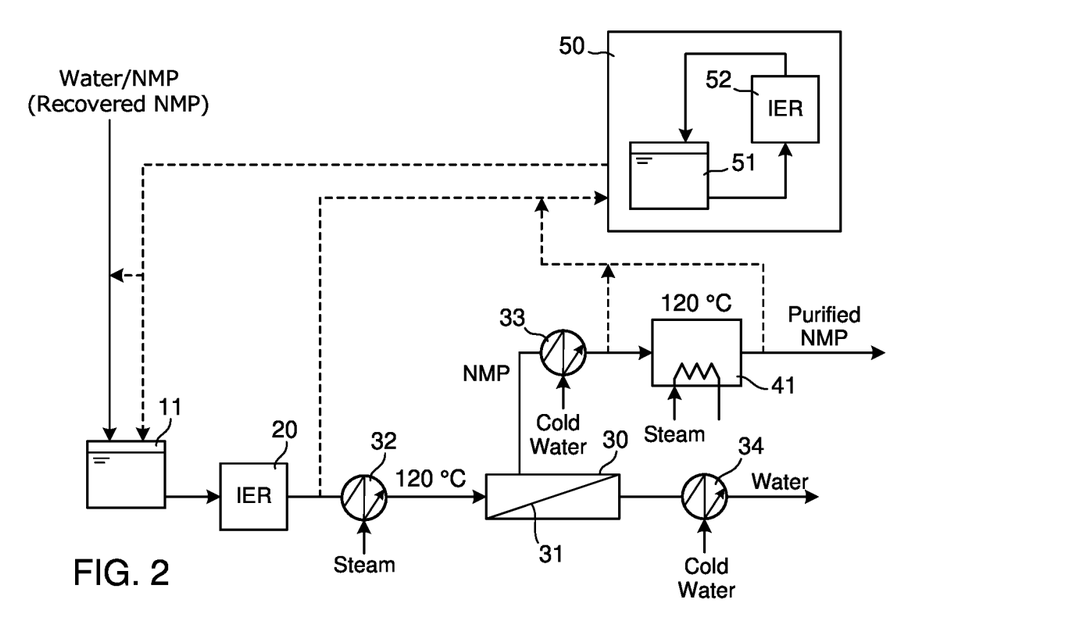
FIG. 2 is a diagram illustrating a purification system of a first embodiment.

FIG. 2 illustrates a purification system of a first embodiment according to the present invention. The purification system shown in FIG. 2 is one in which recovered NMP, which is a liquid mixture of water and NMP, is supplied to discharge purified NMP, and includes: raw solution tank 11 for temporarily storing the recovered NMP; first ion exchange device (IER) 20 in which the recovered NMP is supplied from raw solution tank 11 to perform a first ion exchange process with respect to the recovered NMP; pervaporation device 30 in which the recovered NMP subjected to the ion exchange process by first ion exchange device 20 is supplied to separate water and NMP; and vacuum evaporator 41 in which NMP separated by pervaporation device 30 is supplied. Further, the purification system also includes second ion exchange device 50 that performs a second ion exchange process.

First ion exchange device 20 is filled with an ion exchange resin such as, for example, a styrene-based strongly basic anion exchange resin, similar to that shown in FIG. 1. Between first ion exchange device 20 and pervaporation device 30, heat exchanger 32 is provided for heating the recovered NMP to, for example, 120° C., and steam is supplied as a heat medium to heat exchanger 32. Pervaporation device 30 includes a pervaporation membrane 31 constituted by, for example, zeolite. Water component transmitted through pervaporation membrane 31 and discharged is condensed by condenser 34 to which cold water is supplied as a refrigerant. NMP separated from the recovered NMP is discharged from the concentration side outlet of pervaporation device 30, and is supplied to vacuum evaporator 41 after cooled by heat exchanger 33 to which cold water is supplied as a refrigerant. Vacuum evaporator 41 is for removing hardly-volatile components, such as fine particles and remaining ionic impurities, from NMP. Vacuum evaporator 41 is supplied with steam as a heat medium and maintained at an operating temperature of, for example, 120° C. The inside thereof is reduced in pressure by a pressure reducing means (not shown). As a result, NMP is vaporized to remove hardly-volatile components from NMP, and purified NMP is discharged.

Second ion exchange device 50 is for removing organic impurities such as, for example, N-methylsuccinimide contained in the recovered NMP by ion exchange treatment. For second ion exchange device 50, either of:
(a) a portion of the recovered NMP flowing between the outlet of first ion exchange device 20 and heat exchanger 32;
(b) a portion of NMP flowing between the concentration side outlet of pervaporation device 30 and the inlet of vacuum evaporator 41; and
(c) a portion of the purified NMP discharged from vacuum evaporator 41 and condensed
is supplied. It can be said that the liquid supplied to second ion exchange device 50 is a liquid containing NMP, even in any of cases of (a) to (c). That is, in accordance with the embodiment shown in FIG. 1, a portion of the liquid containing NMP flowing through any of positions B1, C, D is supplied to second ion exchange device 50 also in this first embodiment. Second ion exchange device 50 includes: tank 51; and ion exchange unit (IER) 52. Ion exchange unit 52 is filled with an ion exchange resin similar to that of the ion exchange resin filled in second ion exchange device 50 described using FIG. 1. The liquid supplied to second ion exchange device 50 is temporarily stored in tank 51 and is circulated between tank 51 and ion exchange unit 52 to be subjected to the second ion exchange process. The liquid subjected to the ion exchange process is returned to raw solution tank 11 or a preceding stage side of raw solution tank 11. Examples of the preceding stage side of raw solution tank 11 include, for example, a buffer tank (not shown) provided upstream of raw solution tank 11 with respect to the flow of the recovered NMP. Both raw solution tank 11 and the preceding stage side of raw solution tank 11 correspond to position A in the example shown in FIG. 1.

The entire action of second ion exchange device 50 in the embodiment shown in FIG. 2 is the same as that of second ion exchange device 50 in purification system 60 shown in FIG. 1. Therefore, the residence time in ion exchange unit 52 is set to be longer than the residence time in first ion exchange device 20. In particular, in the present embodiment, the liquid containing NMP supplied to second ion exchange device 50 is stored in tank 51, and the liquid is repeatedly circulated between tank 51 and ion exchange unit 52, so that an effective time for the liquid to stay in ion exchange unit 52 is prolonged and a desired residence time is secured.

When a relatively large amount of liquid containing NMP is intermittently supplied to second ion exchange device 50, the entire amount of the supplied liquid may be stored in tank 51, and the liquid may be circulated between tank 51 and ion exchange unit 52, and then the entire amount of the liquid in tank 51 may be returned to raw solution tank 11 or the preceding stage thereof. Such a processing method is a batch type processing method, and is suitable for a case of, for example, once stopping the production of purified NMP when purity in the purified NMP decreases, and then supplying all of the liquid in the path from raw solution tank 11 to vacuum evaporator 41 at that time to tank 51 to perform the second ion exchange treatment, and returning the treated liquid to raw solution tank 11 or the like to start the production of the purified NMP again. In the batch type processing method, an intermittent operation is performed if the total time includes a period in which the purified NMP is generated, and as a whole, a portion of the liquid containing NMP and flowing at the first position subsequent to the first ion exchange step is processed in the second ion exchange processing step, rather than all of the liquid.

When a liquid containing NMP is continuously supplied to second ion exchange device 50 at a relatively low flow rate, circulation of the liquid between tank 51 and ion exchange unit 52 while guiding the liquid to tank 51 may be continued, and the liquid may be extracted from tank 51 at the same flow rate as the flow rate of the liquid supplied to second ion exchange device 50 and returned to raw solution tank 11 or the preceding stage thereof. Such a processing method is a flow type or a continuous type processing method.

In the purification system shown in FIG. 2, a resistivity meter for measuring conductivity of the liquid supplied to second ion exchange device 50 may be provided at the inlet of second ion exchange device 50. By providing a resistivity meter, it is possible to confirm whether or not ionic impurities have been removed in first ion exchange device 20.

Second Embodiment

Figure 3:
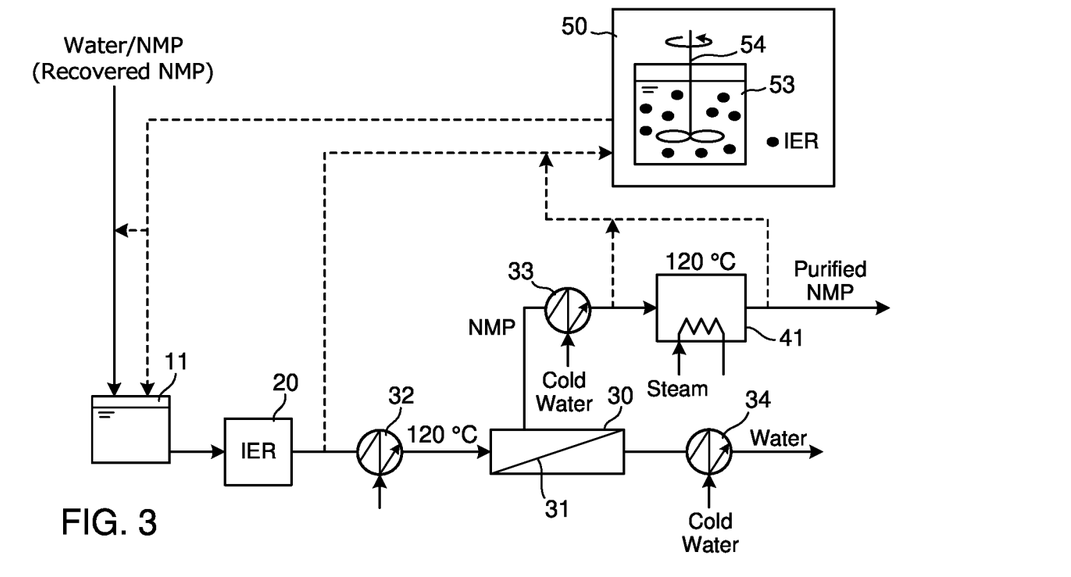
FIG. 3 is a diagram illustrating a purification system of a second embodiment.

FIG. 3 illustrates a purification system of a second embodiment according to the present invention. The purification system shown in FIG. 3 is similar to the purification system of the first embodiment shown in FIG. 2, but in the configuration of second ion exchange device 50 is different from that shown in FIG. 2. Second ion exchange device 50 of the purification system shown in FIG. 3 is provided with tank 53 for storing a liquid containing NMP supplied to second ion exchange device 50. In tank 53, charged is, for example, granulated ion exchange resin (IER). As the ion exchange resin charged into tank 53, the same one as that filled in ion exchange unit 52 in the first embodiment is used. A filter (not shown) is provided in tank 53 so that the ion exchange resin in tank 53 does not flow out to the outside. Tank 53 is also provided with stirring device 54 for stirring the liquid in tank 53 together with the ion exchange resin.

In the purification system of the present embodiment shown in FIG. 3, by stirring the liquid together with the ion exchange resin in tank 53, the same effect as circulating the liquid between tank 51 and ion exchange unit 52 in the purification system of the first embodiment shown in FIG. 2 is obtained. In this embodiment, when a relatively large amount of liquid containing NMP is intermittently supplied to second ion exchange device 50, the entire amount of the supplied liquid may be stored in tank 53, and the liquid may be stirred together with the ion exchange resin in tank 53 for a predetermined time, and then the entire amount of the liquid in tank 53 may be returned to raw solution tank 11 or the preceding stage thereof, as a batch process. In addition, when the liquid containing NMP is constantly supplied to second ion exchange device 50 at a relatively low flow rate, the ion exchange resins may be stirred in tank 53 together with the liquid while guiding the liquid to tank 53, and the liquid may be extracted from tank 53 at the same flow rate as the flow rate of the liquid supplied to second ion exchange device 50 and returned to raw solution tank 11 or the preceding stage thereof. In this case, the residence time is determined by the volume of tank 53 and the flow rate of the liquid to tank 53. The residence time in second ion exchange device 50 in the second embodiment is also set longer than the residence time in first ion exchange device 20.

Also in the purification system shown in FIG. 3, a resistivity meter for measuring conductivity in the liquid supplied to second ion exchange device 50 may be provided at the inlet of second ion exchange device 50. By providing a resistivity meter, it is possible to confirm whether or not ionic impurities have been removed in first ion exchange device 20. Further, although the amount of impurities which can be adsorbed to the ion exchange resin is limited due to saturation in the ion exchange resin, by increasing or decreasing the amount of the ion exchange resin to be charged into tank 53 based on the measured value in the resistivity meter so as to obtain a desired purity, it is possible to reliably perform impurity removal in second ion exchange device 50. Increasing or decreasing the amount of the ion exchange resin to be charged into tank 53 based on the measured value of the resistivity meter makes it possible to easily achieve the target purity in the purified NMP, particularly when a relatively large amount of the liquid is intermittently supplied to second ion exchange device 50 to perform the treatment in a batch manner.

Third Embodiment

Figure 4:
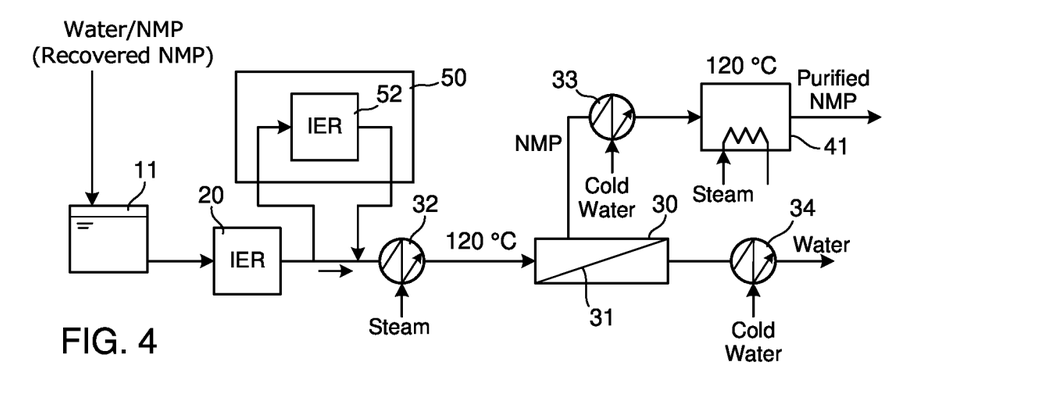
FIG. 4 is a diagram illustrating a purification system of a third embodiment.

FIG. 4 illustrates a purification system of a third embodiment according to the present invention. The purification system shown in FIG. 4 is similar to the purification systems shown in FIGS. 2 and 3, but different from the purification systems shown in FIGS. 2 and 3 in the point that second ion exchange device 50 is composed only of ion exchange unit 52, and another point that a portion of the recovered NMP discharged from first ion exchange device 20 is supplied to second ion exchange device 50 and the recovered NMP processed in second ion exchange device 50 is supplied to the inlet of heat exchanger 32. That is, the purification system of the present embodiment is one concretizing a configuration in which a portion of the recovered NMP flowing through position B1 in purification system 60 shown in FIG. 1 is extracted and guided to second ion exchange apparatus 50 to perform the second ion exchange process, and the recovered NMP subjected to the second ion exchange process is returned to position B2 and supplied to pervaporation device 30. Second ion exchange device 50 is constantly supplied with the recovered NMP at a low flow rate.

In the third embodiment, as the ion exchange resin to be filled in ion exchange unit 52 of second ion exchange device 50, the same as that filled in ion exchange unit 52 in the first embodiment is used. In this embodiment, the recovered NMP supplied to second ion exchange device 50 is supplied to ion exchange unit 52 as it is, and the recovered NMP passed through ion exchange unit 52 merges into the pipe connecting first ion exchange device 20 and heat exchanger 32 as it is. Of the recovered NMP discharged from first ion exchange device 20, the ratio between the portion supplied directly to heat exchanger 32 and the portion supplied to second ion exchange device 50 is set so that the amount of the ion exchange resin filled in ion exchange unit 52 does not become excessive and a sufficient residence time in ion exchange unit 52 is secured. Also in the third embodiment, organic impurities such as, for example, N-methylsuccinimide contained in the recovered NMP are removed in second ion exchange device 50.

REFERENCE EXAMPLES

Hereinafter, experimentations performed by the present inventors in completing the present invention will be described. The present inventors have verified that organic impurities such as, for example, N-methylsuccinimide contained in NMP can be removed by an ion exchange resin. In the following, the results of experimentations targeting an NMP solution which contains N-methylsuccinimide as an organic impurity will be described. Water content refers to the mass ratio of water to the whole NMP solution. Further, NMS ratio refers to the ratio of the mass of N-methylsuccinimide to the sum of the mass of NMP and N-methylsuccinimide in the NMP solution. That is, the NMS ratio refers to the mass ratio of N-methylsuccinimide in the NMP solution when consideration is made except for water component.

Reference Example 1

100 g of an NMP solution containing N-methylsuccinimide of an NMS ratio of 0.058% was prepared, and 1 g of ORLITE® DS-5 manufactured by Organo Corporation, which is a styrene-based MR-type strongly basic anion-exchange resin, was added to the prepared solution, and then stirring was continued. As the NMP solutions, a solution having a water content of 0% and a solution having a water content of 10% were prepared. Then, the mass concentration of N-methylsuccinimide in each NMP solution was quantified by gas chromatography, and its time change was examined. The results are shown in FIG. 5.

Figure 5:
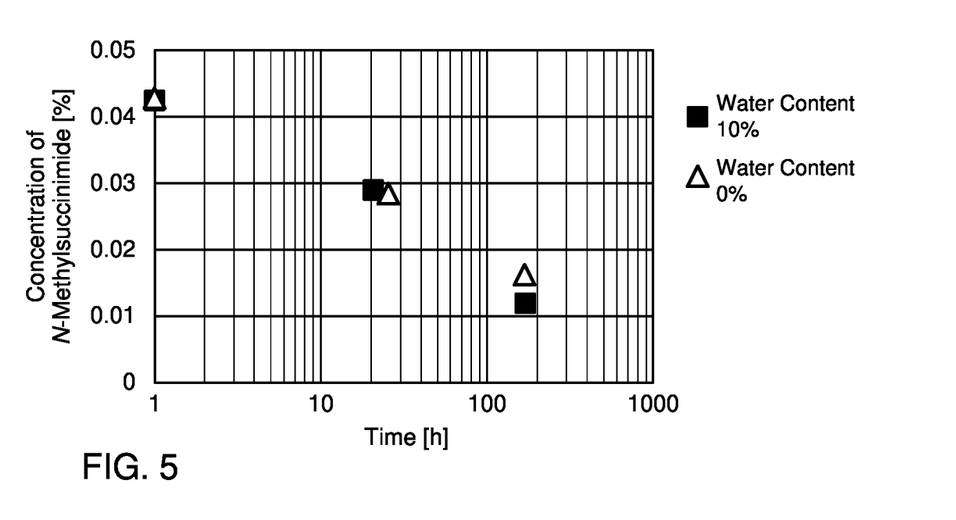
FIG. 5 is a graph showing the results of Reference Example 1.

As shown in FIG. 5, it was found that N-methylsuccinimide in the NMP solution is also adsorbed and removed by the ion exchange resin, and that, if the concentration of N-methylsuccinimide is, for example, 0.1% by mass or less, the adsorption still continues even if it exceeds 100 hours. It was also found that little effect of water content in NMP solution was seen on the adsorption of N-methylsuccinimide.

Reference Example 2

Figure 6:
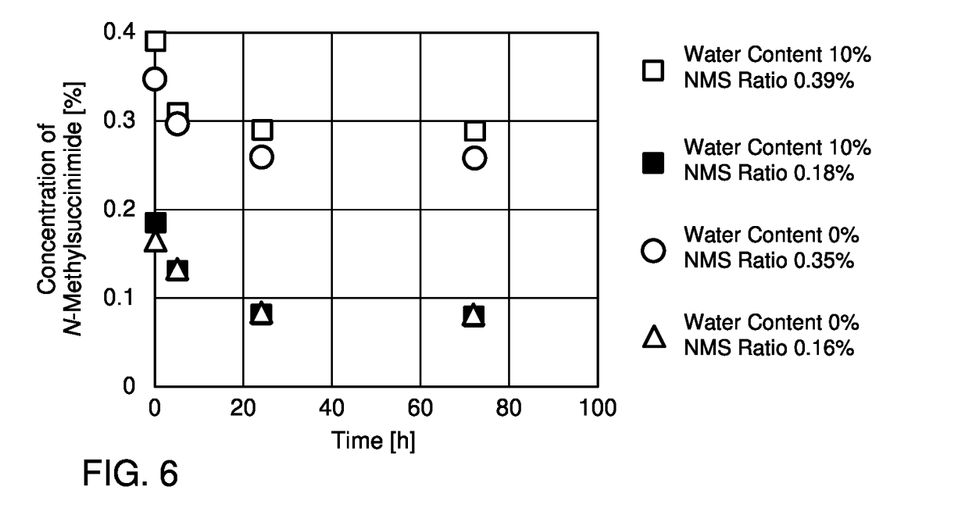
FIG. 6 is a graph showing the results of Reference Example 2.

Four types of NMP solutions were prepared, namely, an NMP solution having an NMS ratio of 0.39% and a water content of 10%; an NMP solution having an NMS ratio of 0.18% and a water content of 10%; an NMP solution having an NMS ratio of 0.35% and a water content of 0%; and an NMP solution having an NMS ratio of 0.16% and a water content of 0%. Each of the NMP solutions was stirred by adding an ion exchange resin in the same manner as in Reference Example 1, and further, the time change of the N-methylsuccinimide concentration in the NMP solution was examined. The results are given in FIG. 6. Reference Example 2 corresponds to a case where the N-methylsuccinimide concentration in the NMP solution is high as compared with Reference Example 1. Even at relatively high concentrations such that the N-methylsuccinimide concentration exceeded 0.1% by mass, the adsorption of N-methylsuccinimide continued even after more than 5 hours.

Reference Example 3

Figure 7:
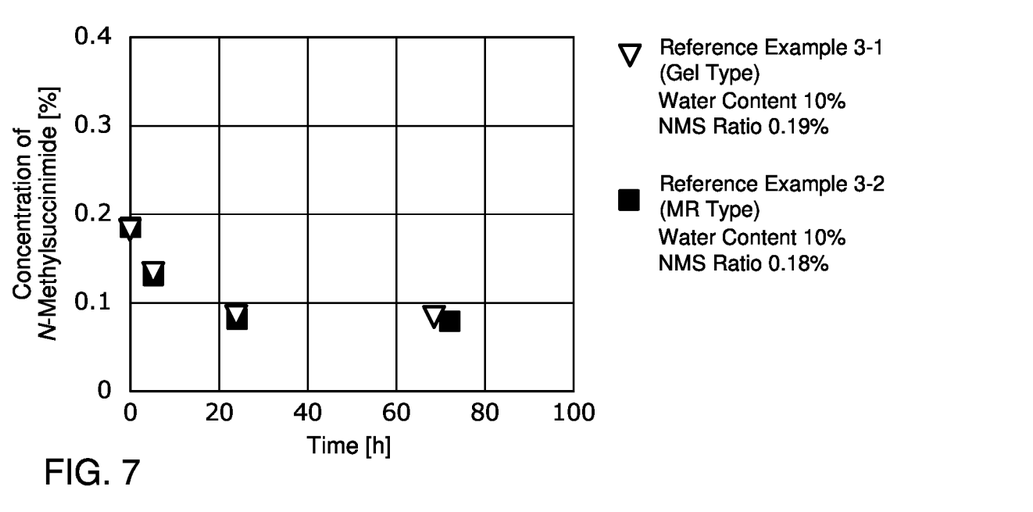
FIG. 7 is a graph showing the results of Reference Example 3.

100 g of an NMP solution containing N-methylsuccinimide having an NMS ratio of 0.19% was prepared, and 1 g of Amberlite® IRA400 (OH) available from Organo Corporation, which is a styrene-based gel-type strong basic anion-exchange resin, was added to the prepared solution, and stirring was continued. The water content of the NMP solution was set to 10%. Then, the mass concentration of N-methylsuccinimide in this NMP solution was quantified by gas chromatography, and its time change was examined. This is referred to as Reference Example 3-1. The results are shown in FIG. 7. For comparison, also illustrated in FIG. 7 as Reference Example 3-2 are the results for the NMP solution having an NMS ratio of 0.18% and a water content of 10% from Reference Example 2, which used an MR-type strongly basic anion-exchange resin. As can be seen from FIG. 7, no major difference occurred depending on whether the structure of the ion exchange resin is MR type or gel type.

| Reference Sign List | |
|---|---|
| 10 | Lithium ion secondary battery (LIB) manufacturing process; |
| 11 | Raw solution tank; |
| 20, 50 | Ion exchange devices; |
| 30 | Pervaporation device; |
| 31 | Pervaporation membrane; |
| 32, 33 | Heat exchangers; |
| 34 | Condenser; |
| 40 | Evaporator; |
| 41 | Vacuum evaporator; |
| 51, 53 | Tanks; |
| 53 | Ion exchanger unit; |
| 54 | Stirring device; |
| 60 | Purification system. |

The invention claimed is:

1. A purification method for separating and purifying an organic solvent from a liquid mixture of the organic solvent and water, the organic solvent having a boiling point of more than 100° C. at 1 atm, the purification method comprising:
a first ion exchange step of passing the liquid mixture into a first ion exchange resin;
a dehydration step of selectively separating water component from the liquid mixture by supplying the liquid mixture discharged from the first ion exchange step to a pervaporation device having a pervaporation membrane;
an evaporation step of supplying the organic solvent recovered from a concentration side of the pervaporation membrane to an evaporator to vaporize, and obtaining the organic solvent which has been purified; and
a second ion exchange step of treating a portion of liquid which contains the organic solvent that flows into a branch point at a first position, and
wherein liquid discharged from the second ion exchange step is returned to a second position,
wherein the first position is:
located between the concentration side of the pervaporation membrane and an inlet of the evaporator,
located between an outlet of the first ion exchange step and an inlet of the pervaporation device, and prior to the second position, and/or
at a position at which the organic solvent discharged from the evaporation step flows, and
wherein the second position is located between the outlet of the first ion exchange step and an inlet of the dehydration step.

2. The purification method according to claim 1, wherein in the second ion exchange step, liquid supplied to the second ion exchange step is circulated between an ion exchange unit filled with the second ion exchange resin and a tank.

3. The purification method according to claim 1, wherein, in the second ion exchange step, liquid supplied to the second ion exchange step is stirred together with the second ion exchange resin in a tank into which the second ion exchange resin is charged.

4. The purification method according to claim 1, wherein, in the second ion exchange step, liquid supplied to the second ion exchange step is passed through an ion exchange unit filled with the second ion exchange resin, and the liquid discharged from the ion exchange unit is returned to the second position.

5. The purification method according to claim 1, comprising a step of measuring conductivity of liquid supplied to the second ion exchange step.

6. A purification system for separating and purifying an organic solvent from a liquid mixture of the organic solvent and water, the organic solvent having a boiling point of more than 100° C. at 1 atm, the purification system comprising:
a first ion exchange device to which the liquid mixture is supplied;
a pervaporation device having a pervaporation membrane in which the liquid mixture passed through the first ion exchange device is supplied to selectively separate water component from the liquid mixture;
an evaporator vaporizing the organic solvent recovered from a concentration side of the pervaporation membrane and generating the organic solvent which has been purified; and a second ion exchange device fluidly connected to a branch point at a first position,
wherein liquid discharged from the second ion exchange device is returned to a second position,
wherein the first position is:
    located between the concentration side of the pervaporation membrane and an inlet of the evaporator,
    located between an outlet of the first ion exchange device and an inlet of the pervaporation device, and is prior to the second position, and/or
    at a position at which the organic solvent discharged from the evaporator flows, and
wherein the second position is located between the outlet of the first ion exchange device and the inlet of the pervaporation device.

7. The purification system of claim 6, wherein the second ion exchange device comprises: a tank; and an ion exchange unit filled with ion exchange resin, and wherein liquid supplied to the second ion exchange device circulates between the tank and the ion exchange unit.

8. The purification system according to claim 6, wherein the second ion exchange device comprises: a tank into which an ion exchange resin is charged; and a stirring device which stirs inside of the tank, and wherein liquid supplied to the second ion exchange device is stirred together with the ion exchange resin in the tank.

9. The purification system according to claim 6, wherein the second ion exchange device comprises an ion exchange unit which is filled with ion exchange resin and through which liquid supplied to the second ion exchange device is passed, and wherein liquid discharged from the ion exchange unit is returned to the second position.

10. The purification method according to claim 1, comprising means for measuring conductivity of liquid supplied to the second ion exchange device, the means is provided at an inlet of the second ion exchange device.

11. The purification method according to claim 2, comprising a step of measuring conductivity of the liquid supplied to the second ion exchange step.

12. The purification method according to claim 3, comprising a step of measuring conductivity of the liquid supplied to the second ion exchange step.

13. The purification method according to claim 4, comprising a step of measuring conductivity of the liquid supplied to the second ion exchange step.

14. The purification system according to claim 7, comprising means for measuring conductivity of liquid supplied to the second ion exchange device, the means is provided at an inlet of the second ion exchange device.

15. The purification system according to claim 8, comprising means for measuring conductivity of liquid supplied to the second ion exchange device, the means is provided at an inlet of the second ion exchange device.

16. The purification system according to claim 9, comprising means for measuring conductivity of liquid supplied to the second ion exchange device, the means is provided at an inlet of the second ion exchange device.

* * * * *